United States Patent [19]
Huffman

[11] 3,937,773
[45] Feb. 10, 1976

[54] METHOD OF CONSTRUCTING DENTAL MODELS USING GUIDE PINS AND APERTURED RETAINER

[75] Inventor: Ronald E. Huffman, Tucson, Ariz.

[73] Assignee: KV33 Corporation, Tucson, Ariz.

[22] Filed: Mar. 4, 1974

[21] Appl. No.: 448,070

[52] U.S. Cl. .................... 264/17; 264/69; 264/71; 264/154; 264/222; 264/261; 264/333; 32/11
[51] Int. Cl.² .................. A61C 13/00; B28B 1/08; B32B 31/18
[58] Field of Search ........................... 264/16–18, 264/69, 71, 261, 154, 222; 32/11

[56] References Cited
UNITED STATES PATENTS

| | | | |
|---|---|---|---|
| 3,226,827 | 1/1966 | Spalten | 32/11 |
| 3,413,725 | 12/1968 | Stern et al. | 32/11 |
| 3,478,428 | 11/1969 | Stengel | 32/11 |

Primary Examiner—Robert F. White
Assistant Examiner—Willard E. Hoag
Attorney, Agent, or Firm—Cahill, Sutton & Thomas

[57] ABSTRACT

In a dental model, a plurality of parallel non-tapered guide pins are slidably seated within cylindrical cavities in an apertured retainer. Extending sections of the guide pins are secured within removable cast teeth, whereby the guide pins and their mating cavities permit withdrawal and replacement of the removable cast teeth while maintaining the alignment of the removable cast teeth with respect to the dental model.

3 Claims, 7 Drawing Figures

METHOD OF CONSTRUCTING DENTAL MODELS USING GUIDE PINS AND APERTURED RETAINER

The present invention relates to dental models, and, more particularly, to guide pins and the seating thereof in dental models.

In the field of dentistry, false teeth are often retained in place by means of bridge work extending from the false tooth and anchored to adjacent healthy teeth. Other restoration techniques includes the capping of badly decayed or deformed teeth with either a full or a partial cap.

To accurately form and position the false teeth or caps, a dentist normally makes a negative impression of the affected teeth. The negative impression may be partial, unilateral or bilateral, depending upon the extent of work to be done, and serves as a mold for developing a die of the patient's teeth.

Pursuant to the teaching of the prior art, the die may be formed in the following manner. A plurality of tapered dowels are positioned within the negative impression to correspond with the center of each cavity, which cavity represent an existing tooth. These dowels may be maintained in place by means of a plurality of positioning pins, as shown in U.S. Pat. No. 3,521,354. In the alternative, a jig assembly such as shown in U.S. Pat. No. 2,851,728, may be used to properly position and orient the various dowels. To avoid the necessity for external and removable positioning pins or alignment devices, an alignment plate may be inserted within the negative impression, as described in U.S. Pat. No. 3,470,614. The alignment plate is permanently retained within the to-be-cast die and includes a dowel protruding therefrom to maintain alignment of the segregated cast teeth.

In an effort to overcome the need for external aligning mechanisms and devices, several alternatives have been developed. U.S. Pat. No. 3,286,350, teaches the insertion of individual dowels within each of the cavities of the impression. These pins must be manually aligned during the setting of the die compound. U.S. Pat. No. 3,478,428, teaches a base having a plurality of parallel tapered dowels extending upwardly therefrom. Here, the base is laid within the negative impression such that each of the pins extends into the die compound disposed within the negative impression.

After each of the above described dowels or dowel assemblies have been mounted within the negative impression such that at least a portion of the dowels extend into the cavities representing the existing teeth, a die compound or pourable curable stone is poured into the impression until the latter is filled to a point approximating the patient's gum line. Thereby, at least a portion of each of the dowels is immersed within the poured stone and becomes a part thereof during the curing process. After curing, a wax or similar material is placed upon the stone surface. A further amount of die compound is then poured upon the cured stone to immerse the remaining parts of the dowels and form a base for the assembly.

After the two resulting stone molds have cured, the negative impression is removed. The composite mold structure is an exact duplication of the patient's teeth and the upper part of his gum. Removal of an individual tooth to prepare bridework on a cap is accomplished by making vertical cuts on either side of the affected tooth beyond the intersection of the two stone molds. The wax or similar material inserted intermediate the two poured stones permits facile separation therebetween such that the tooth may be easily severed from the base. The dowels extending downwardly from the tooth into the base, are smooth surfaced and tapered such that they may be easily broken loose from the base. Thereby, the tooth may be easily removed from the base and reinserted therein in a laterally correct position when the dowel is fully seated.

In each of the above referenced patents, the alignment dowels are tapered. The taper allows dirt or other contaminates to impede complete seating of the tooth. Without complete seating, the tooth may not be correctly positioned. Repeated insertion and removal of the alignment dowels will tend to loosen the dowel cavity resulting in a sloppy fit.

The prior art requirements for alignment of the pins is time consuming and is primarily dependent upon the skill of the particular dental technician, which may result in a high percentage of defective castings. Moreover, the prior art techniques do not automatically assure parallelism between the dowel pins. The lack of parallelism may result in difficulty when the selected tooth or teeth to be worked upon are to be removed.

It is therefore a primary object of the present invention to provide a plurality of pre-aligned parallel guide pins for use in dental models.

Another object of the present invention is to obviate the need for manually aligning guide pins parallel to one another when constructing a dental model.

Yet another object of the present invention is to provide a plurality of non-tapered guide pins for use in dental models.

Still another object of the present invention is to provide guide pins for removable cast teeth in a dental model wherein the lateral position of the cast teeth is not dependent upon the complete seating of the teeth.

A further object of the present invention is to provide a plurality of guide pins oriented parallel to one another which may be inserted within a dental impression without extraneous guide and alignment members.

A yet further object of the present invention is to provide self-cleaning guide cavities for guide pins within a dental model.

A still further object of the present invention is to provide a wear resistant precision fit between parallel guide pins and a retainer member thereof in dental models.

These and other objects of the present invention will become apparent to those skilled in the art as the description thereof proceeds.

The present invention may be described with greater specificity and more clarity with reference to the following figures, in which.

Figure 1:
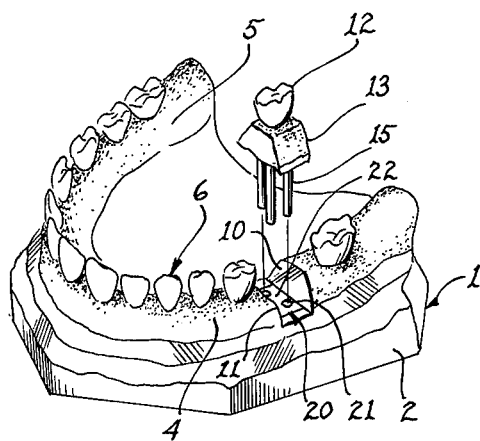
FIG. 1 illustrates a perspective view of a dental model incorporating the present invention.

Referring to FIG. 1, there is shown a perspective view of a dental model 1 constructed in accordance with the teachings of the present invention. The dental model 1 includes a base 2 formed of readily commercially available pourable casting stone. The die 3, duplicating a patient's teeth and associated gum structure, is also formed of similar casting stone material. For completeness, die 3 includes a part of the buccal and lingual walls, 4 and 5, as well as each of the existing teeth 6.

For illustrative purposes, a single tooth 12 and its associated gum section 13 has been severed from the die 3 by mesial and distal cuts, 10 and 11. These cuts have been made downwardly through die 3 to intersect the junction intermediate base 2 and the die. A plurality of guide pins 15 extend downwardly from the gum section 13. These guide pins 15 mate with and are received by cylindrical cavities 21 disposed within a retainer 20. The latter is imbedded within base 2 during the dental model forming process such that its upper surface 22 is disposed in approximate alignment with the junction intermediate base 2 and die 3.

To further illustrate the retainer 20 and its associated guide pins 15 with respect to dental model 1, reference will be made to FIG. 2. Retainer 20 is generally rectangular in cross-section and includes a plurality of rows of cylindrical cavities 21. A guide pin 15 is slidably insertable within each of cavities 21. In the preferred embodiment, retainer 20 is constructed of nylon or similar low friction stable material; the guide pins 15 are smooth surfaced and of metallic material such that they can easily slide within their respective cavity 21. Guide pins 15 are of greater length than the height of retainer 20 such that the upper extending section 19 can be flattened into a spade 25 having a serrated surface 26. Alternatively, the upper section 19 may be retained cylindrical with its surface serrated, or other means may be employed to obtain a structural interlocking relationship between the upper section 19 and the surrounding material of die 3. The lower extremity of each of guide pins 15 may extend downwardly beneath the lower surface 27 of retainer 20 for 1/16 of an inch or more.

Retainer 20 is positioned within base 2 such that the upper surface 22 of the retainer is approximately coincident with the line of demarcation 17 between base 2 and die 3.

During the formation of base 2 and die 3, the two parts are poured separately and wax or other similar lubricant is applied at the junction of the two pours such that there will be little if any physical adherence between base 2 and die 3. Thereby, only the mesial and distal cuts are necessary to separate a longitudinal segment of die 3 from the adjoining base.

As retainer 20 is preferably made of nylon or other similar low friction material, it becomes incumbent to provide some means whereby the retainer is permanently lodged or positioned within base 2. By providing retainer 20 with a plurality of transverse ribs 24, movement of the retainer in the vertical axis in inhibited. These ribs may extend along the sides of retainer 20 and along the ends thereof (see FIG. 3). Ribs 24 may be dovetail shaped in cross-section as illustrated, or they may be of simple rectangular configuration. In either case, they will physically lock retainer 20 within base 2 to inhibit any movement along the axis of guide pins 15.

Figure 3:
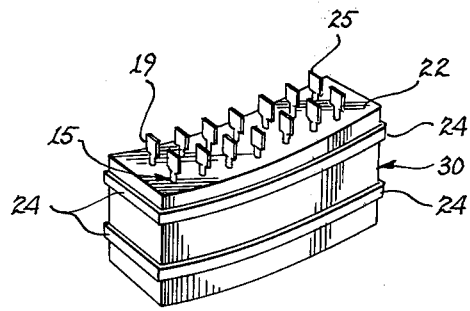
FIG. 3 illustrates a short curved section of the retaining base for the guide pins of the present invention.

FIG. 3 illustrates a retainer 20 configured as a short curved element 30 having a rectangular cross-section. Such an element may be employed where the dentist or dental laboratory technician wishes to prepare bridge work extending across only one or two missing teeth. The guide pins 15 may be arranged by columns in two parallel rows as shown, or, the guide pins of one row may be off-set with those of the adjacent row. The selection by number and spacing of pins is primarily dependent upon the size of the teeth to be worked upon such that at least one, and preferably several, guide pins are coincident with each of the teeth embodied in die 3. It may be appreciated by those skilled in the art that if two or more pins are associated with each tooth, not only will the tooth be laterally positioned but angular misalignment about the vertical axis will also be precluded.

Should the mesial or distal cuts be coincident with one or more guide pins 15, the latter will be cleaned or severed by the cuts. Thereby, the pre-formation of the retainer 20 and guide pins 15 will accommodate any cuts to be made by a dental technician.

Figure 4:
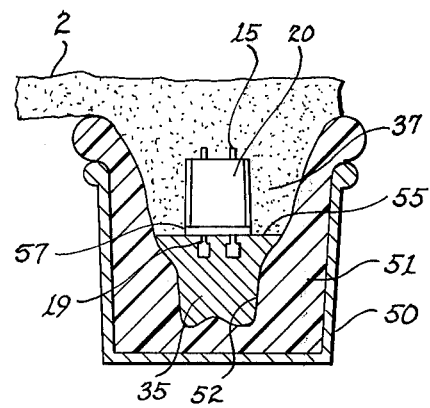
FIG. 4 illustrates a cross-sectional view of the present invention inserted within a mold during the dental model forming process.

The process for using the present invention is illustrated in FIG. 4. A negative impression of the patient's teeth is obtained by partially filling a tray 50 with thermoplastic material 51. The filled tray is inserted within the patient's mouth such that the teeth and adjacent gums sink into and create a mold cavity within the thermoplastic material. Shortly thereafter, the thermoplastic material will cure and retain an exact impression of the patient's teeth and gums. This is an essentially standard technique presently used by most dentists.

To form the base 2 and die 3 (as shown in FIG. 1), the following process may be employed. A pourable casting stone, known as "pink stone" 35 amongst the cognoscente, is poured into the negative impression up to at least the "margin" 36 or base of the tooth to form die 3. After the pink stone 35 has been compacted to preclude voids and remove any air bubbles, retainer 20, including the guide pins 15 inserted therein, is placed upon the surface 55 of the pink stone 35 such that the extending sections 19 protrude into the pink stone below the margin 36. Preferably, the degree of extension of the guide pins 15 is such that the upper surface 22 of retainer 20 lies upon the surface 55. After the pink stone 35 is at least partially cured, wax or similar lubricant is swathed upon surface 55. Thence, additional pourable hardenable stone, generally referred to as "yellow stone" 37, is poured within the negative impression 52 to cover the pink stone 35 and retainer 20 with sufficient additional material to form a solid base 2. After the pink and yellow stone has hardened, the tray 50 is removed and the thermoplastic material 51 is peeled away to leave the dental model 1 as shown in FIG. 1.

When the mesial and distal cuts are made down through the line of demarcation 17 between the pink and yellow stone, the pink stone 35 will easily separate from the yellow stone 37 because of the previously applied wax or lubricant. As retainer 20 is of nylon or similar low friction non-adhering material, the pink stone 35 will easily sever therefrom also. The spade or serrated ends of guide pins 15 are firmly embedded within the pink stone 35 and as a section of the latter is lifted (see FIG. 1), the guide pins will be withdrawn from within retainer 20.

As mentioned above, the guide pins are cylindrical whereby the removed section of die 3 is laterally positioned with respect to the remaining part of the die on initial engagement of guide pins 15 with their respective cavities 21. If more than one guide pin extends from the removed section, the angular orientation of the removed section is immediately reestablished and easily duplicatable whenever the guide pins are reinserted within their respective cavities.

As all of the guide pins are formed within retainer 20 parallel to one another, two removable sections adjacent one another can be removed simultaneously or in any sequence without obstruction from adjacent removable sections.

Where base 2 is cut away or formed essentially coincident with the lower surface 27 of retainer 20, any dirt or impurity which may have lodged itself within cavities 21 will be pushed out therefrom by the insertions of guide pins 15 therein. Thereby, dirt or other particulate matter will not destroy the alignment or proper seating of the removable section. Moreover, if the guide pins 15 extend below surface 27 they can be lightly tapped to initially dislodge the cut section from the die 3.

Although not immediately apparent, the present invention permits adjacent normally contacting teeth to be maintained in contact with one another during the insertion of the removable sections. This feature greatly simplifies the forming of inlays or similar prosthetic items which are at least partly located in juxtaposition with adjacent teeth. It allows the formation and manufacture of these inlays so that they can be mounted upon the patient's tooth with a straight vertical movement while compensating for overhang by adjacent teeth. This feature is not available from prior art techniques as none of them are completely laterally and rotationally position the removable cast teeth until they are fully seated. Thus, with the prior art devices, the existence of the overhand may not be evident until the inlay is to be mounted upon the patient's tooth.

As shown in cross-section in FIG. 4, the part of retainer 20 adjacent the pink stone 35 may include a peripheral flange 57 to provide additional support to prevent the retainer from sinking into the pink stone. It also serves to provide a greater surface area and an angularly configured surface to more firmly seat the retainer 20 within the yellow stone 37.

Figure 5:
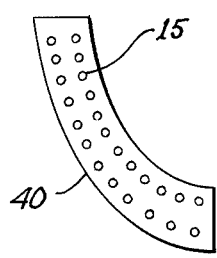
FIG. 5 illustrates the retaining base preformed on a unilateral configuration.
Figure 6:
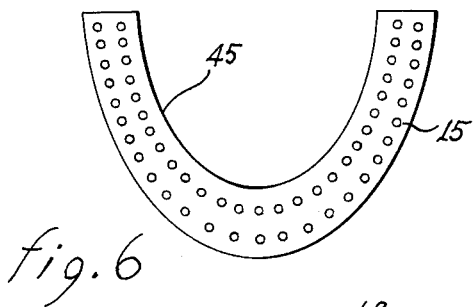
FIG. 6 illustrates the retaining base preformed in a bilateral configuration.

FIGS. 5 and 6 illustrates a unilateral element 40 and a bilateral element 45. These elements may be employed in preference to element 30 shown in FIG. 3 where extensive work is to be performed on one half of the patient's jaw or upon the full jaw. Again, two or more rows of guide pins 15 are disposed within each of elements 40 and 45 in order that at least one pin be in alignment with every tooth, regardless of the size or position of the tooth.

Figure 2:
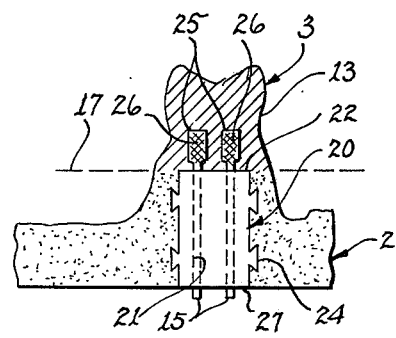
FIG. 2 illustrates a cross-sectional view of a dental model incorporating the present invention.
Figure 7:
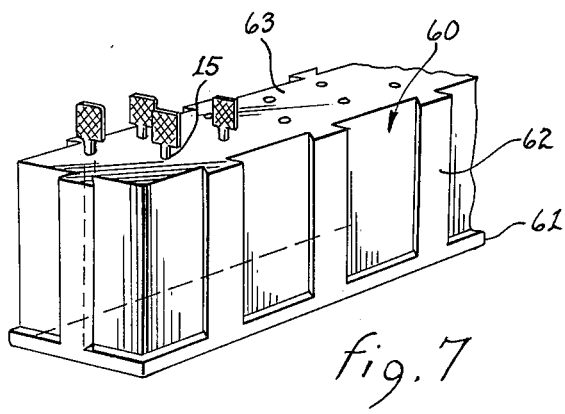
FIG. 7 illustrates a perspective view of a retaining base having a modified external surface.

As shown in FIG. 2, the retainer 20, particularly if configured as unilateral or bilateral elements 40, 45 shown in FIGS. 5 and 6, may be employed without the necessity for adding the yellow stone 37 to form base 2. In this case, the length of retainer 20 is selected to extend beyond the area to be worked upon such that the extending sections 19 of guide pins 15 are firmly locked within the adjacent sections of pink stone 35. The rigidity of the guide pins 15, as provided by retainer 20, is sufficient to maintain the adjacent sections of the die 3 in alignment with one another despite removal of the centrally located removable sections.

Where a base 2 (see FIGS. 1 and 2) is to be employed but where it is desired that the lower surface 27 of retainer 20 is to be exposed to facilitate cleaning of cavities 21, a configuration for the retainer as shown in FIG. 7 may be employed. Retainer 60 includes one or more rows of guide pins 15 inserted therein. The external surface of retainer 60 includes an outwardly extending flange 61 disposed at the lower periphery. A plurality of ribs 62, which may be dovetailed in cross-section, extend upwardly from flange 61 and terminate at a plane defined by the upper surface 63 of retainer 60. Flange 61 prevents retainer 60 from being drawn through base 2 (see FIG. 2) as the removable sections are pulled upwardly therefrom. The multiangular surfaces of flange 61 also aids in firmly seating retainer 60 within base 2. The vertically extending ribs 62 provide a physical interlock with base 2 to prevent lateral movement of the retainer. It is to be understood that other flange and/or rib configurations may be employed to meet special and/or particular needs for lodging the retainer within the base.

In summary, the present invention provides a retainer having a plurality of parallel preformed guide pins slidably mounted therein. Thereby, all of the alignment devices and problems associated with prior art techniques are completely obviated. As the guide pins are cylindrical and seat within mating cavities, the removable sections are laterally postioned on initial engagement of the pins within the respective cavities. Where more than one guide pin is associated with each removable section, the removable section is angularly aligned in the vertical axis immediately upon engagement of the guide pins with their respective cavities. As all of the cavities for receiving the guide pins are formed parallel to one another, simultaneously insertion or removal of multiple guide pins is not impeded or restricted due to guide pin misalignment, as is common with prior art devices. In the seated position, the guide pins may extend through their respective cavities, which permits the guide pins to perform a self cleaning function in removing dirt or other particulate matter accidentally lodged within the respective cavities. The structural integrity of the retainer permits a technician to circumvent the pouring of the base, or yellow stone, without comprising the structural or positional integrity of the impression.

While the principles of the invention have now been made clear in an illustrative embodiment, there will be immediately obvious to those skilled in the art many modifications of structure, arrangement, proportions, the elements, materials, and components, used in the practice of the invention which are particularly adapted for specific environments and operating requirements without departing from those principles.

I claim:

1. A method for forming a dental model with cast teeth which are selectively detachable and replaceable, the model being formed from a negative impression of a plurality of teeth, which negative impression includes buccal and lingual walls and wherein an uncured casting stone is poured into the negative impression to a depth sufficient to include margins, the teeth being removable and insertable while maintaining their alignment, said method comprising the steps of:

a. using a retainer having a plurality of parallel transversely oriented cylindrical cavities and of a length and configuration commensurate with the type and number of cast teeth to be removed from and inserted into the dental model;

b. removably inserting the body of each of a plurality of non-tapered guide pins into a mating one of the cylindrical cavities extending through the retainer, each of the guide pins having a perturbation disposed at one end thereof;

c. positioning the guide pins within the retainer to maintain the perturbed end of each of the guide pins external to the retainer;

d. locating the retainer adjacent the uncured casting stone to fully immerse the perturbed ends of the guide pins within the casting stone;

e. compacting the casting stone to fill any voids within the negative impression and to remove any air bubbles;

f. curing the casting stone to form a rigid composite assembly of casting stone and the perturbed ends of the guide pins, which assembly terminates at a nearer surface of the retainer; and g. making mesial and distal cuts through the cured casting stone only to the surface of the retainer from which the perturbed ends of the guide pins extend to segregate a section of casting stone defining at least one cast tooth and having at least the perturbed end of one guide pin lodged therein but leaving the retainer intact; whereby, the guide pin or guide pins extending from the section and being non-tapered and slidably retained within the cylindrical cavities of the retainer prevent wobble and tilting of the section during removal and reinsertion thereof.

2. The method as set forth in claim 1 further including the steps of:

a. swathing the surface of the casting stone with a lubricant; and b. further pouring casting stone within the negative impression to cover the first poured casting stone and encase the retainer.

3. The method as set forth in claim 2 further including the step of yet further pouring casting stone to form a base for the dental model.

* * * * *